(12) United States Patent
Shim et al.

(10) Patent No.: US 8,648,178 B2
(45) Date of Patent: Feb. 11, 2014

(54) METHOD FOR PURIFYING BONE MORPHOGENETIC PROTEIN

(75) Inventors: Young-Bock Shim, Seoul (KR); Yeong-Schick Kim, Gyeonggi-do (KR); Yon-Rak Choi, Gyeonggi-do (KR); Ju-Woong Jang, Seoul (KR)

(73) Assignee: Korea Bone Bank Co., Ltd. (KR)

( * ) Notice: Subject to any disclaimer, the term of this patent is extended or adjusted under 35 U.S.C. 154(b) by 0 days.

(21) Appl. No.: 13/142,928

(22) PCT Filed: May 12, 2010

(86) PCT No.: PCT/KR2010/003021
§ 371 (c)(1),
(2), (4) Date: Jun. 30, 2011

(87) PCT Pub. No.: WO2011/142490
PCT Pub. Date: Nov. 17, 2011

(65) Prior Publication Data
US 2013/0060012 A1    Mar. 7, 2013

(30) Foreign Application Priority Data
May 10, 2010   (KR) .................. 10-2010-0043673

(51) Int. Cl.
C07K 14/51 (2006.01)
C07K 1/14 (2006.01)
C07K 1/16 (2006.01)
C07K 1/34 (2006.01)
C07K 1/36 (2006.01)

(52) U.S. Cl.
USPC ........... 530/399; 530/412; 530/414; 530/415; 530/417

(58) Field of Classification Search
None
See application file for complete search history.

(56) References Cited

U.S. PATENT DOCUMENTS

2003/0036629 A1*   2/2003   Foster et al. .................. 530/344

OTHER PUBLICATIONS

Yoshimura et al., Biol. Pharm. Bull., 1993, vol. 16(5):444-447.*
A. Suzuki, E. Kaneko, J. Maeda and N. Ueno, "Mesoderm induction by BMP-4 and -7 heterodimers," Biochem. Biophys. Res. Commun., vol. 232, pp. 153-156, Mar. 1997.
K. Azari, B. A. Doll, C. Stair, Y. Mu and J. O. Hollinger, "Therapeutic potential of bone morphogenetic proteins," Expert Opinion on Investigational Drugs, vol. 10, pp. 1677-1686, Sep. 2001.
D. I. Israel, J. Nove, K. M. Kerns, I. K. Moutsatsos and R. J. Kaufman, "Expression and Characterization of Bone Morphogenetic Protein-2 in Chinese Hamster Ovary Cells" Growth Factors, vol. 7, pp. 139-150, 1992.
D. I. Israel, J. Nove, K M. Kerns, R. J. Kaufman, V. Rosen, K. A. Cox and J. M. Wozney, "Heterodimeric bone morphogenetic proteins show enhanced activity in vitro and in vivo," Growth Factors, vol. 13, pp. 291-300, 1996.
P. J. Marie, F. Deibais, E. Hay, "Regulation of human cranial osteoblast phenotype by FGF-2, FGFR-2 and BMP2 signaling", Histol. Histopathol., vol. 17, pp. 877-885, 2002.
M. F. Mehler, P. C. Mabie, D. M. Zhang and J. A. Kessler, "Bone morphogenetic proteins in the nervous system," Trends Neurosci., vol. 20, pp. 309-317, 1997.
T. K. Sampath, J. E. Coughlin and R. M. Whetstone, "Bovine osteogenic protein is composed of dimers of OP-1 and BMP-2A, two members of the transforming growth factor-b superfamily," J. Biol. Chem, vol. 265, pp. 13198-13205, Aug. 1990.

* cited by examiner

Primary Examiner — Xiaozhen Xie
(74) Attorney, Agent, or Firm — Levenfeld Pearlstein, LLC

(57) ABSTRACT

The present invention relates to a method for purifying a protein belonging to the TGF-β, superfamily, preferably BMP, and more preferably BMP-2. According to the invention, the number of purification steps is reduced and the purification process is simplified, compared to the conventional BMP-2 purification method. Thus, the time required for purification can be shortened and the cost can be reduced. In addition, the invention solves the problem that as the time for purification increases and the number of purification steps increases, BMP-2 is degraded by protease or lost during purification steps, resulting in a decrease in the final yield of BMP-2. Thus, the invention increases the final yield of BMP-2. In addition, according to the invention, although the number of purification steps is reduced, BMP-2 having high purity is obtained in high yield by optimizing and using filtrations and chromatographies, and columns, types and concentrations of buffers, and a cut-off size of membrane used in diafiltration, which are different from those of the conventional BMP-2 purification method.

15 Claims, 4 Drawing Sheets

METHOD FOR PURIFYING BONE MORPHOGENETIC PROTEIN

CROSS-REFERENCE TO RELATED APPLICATIONS

This is a National Stage Application of International Patent Application No. PCT/KR2010/003021, filed May 12, 2010, which claims the benefit of and priority to Korean Patent Application No. 10-2010-0043673, filed May 10, 2010, the contents of each of which are incorporated fully by reference herein.

TECHNICAL FIELD

The present invention relates to a method for purifying a protein belonging to the transforming growth factor-β (TGF-β) superfamily, preferably a bone morphogenetic protein (BMP), and more preferably a bone morphogenetic protein 2 (BMP-2). Also, the present invention relates to a protein belonging to the TGF-β superfamily, preferably a BMP, and more preferably a BMP-2, purified in high purity and high yield according to said method.

BACKGROUND ART

Bone morphogenetic proteins (BMPs) belong to the TGF-βsuperfamily of the secreted growth and differentiation factors. The BMP subfamily of the TGF-β superfamily includes at least fifteen proteins, including BMP-2, BMP-3, BMP-3b, BMP-4, BMP-5, BMP-6, BMP-7, BMP-8, BMP-9, BMP-10, BMP-11, BMP-12, BMP-13, BMP-14 and BMP-15.

It has been reported that BMPs regulate the growth and differentiation of cells such as osteogenic cells, and particularly BMP-2, BMP-4, BMP-5, BMP-6, BMP-7 and BMP-8 are growth and differentiation factors that can induce ectopic bone formation alone in vitro and in vivo. Also, BMP-2 can direct the development of neural crest cells into neural phenotypes, and BMP-4 and BMP-7 can induce a sympathetic adrenergic phenotype. It has been reported that a heterodimer composed of BMP-4 and BMP-7 is a potent inducer of mesoderm (see A. Suzuki, E. Kaneko, J. Maeda and N. Ueno, "Mesoderm induction by BMP-4 and -7 heterodimers," Biochem. Biophys. Res. Commun., vol. 232, pp. 153-156, March 1997).

In addition, BMPs can form either homodimers composed of monomers of a single BMP subfamily member or heterodimers composed of monomers of two different BMP subfamily members linked by a disulfide bond in a head-to-tail arrangement (see K. Azari, B. A. Doll, C. Sfeir, Y. Mu and J. O. Hollinger, "Therapeutic potential of bone morphogenetic proteins," Expert Opinion on Investigational Drugs, vol. 10, pp. 1677-1686, September 2001). Also, it was reported that BMP dimers such as BMP-2 homodimers and BMP-2/7 heterodimers are active in vivo (see D. I. Israel, J. Nove, K. M. Kerns, I. K. Moutsatsos and R. J. Kaufman, "Expression and Characterization of Bone Morphogenetic Protein-2 in Chinese Hamster Ovary Cells," Growth Factors, vol. 7, pp. 139-150, 1992; M. F. Mehler, P. C. Mabie, D. M. Zhang and J. A. Kessler, "Bone morphogenetic proteins in the nervous system," Trends Neurosci., vol. 20, pp. 309-317, 1997; T. K. Sampath, J. E. Coughlin and R. M. Whetstone, "Bovine osteogenic protein is composed of dimers of OP-1 and BMP-2A, two members of the transforming growth factor-b superfamily," J. Biol. Chem., vol. 265, pp. 13198-13205, August 1990; D. I. Israel; J. Nove, K. M. Kerns, R. J. Kaufman, V. Rosen, K. A. Cox and J. M. Wozney, "Heterodimeric bone morphogenetic proteins show enhanced activity in vitro and in vivo," Growth Factors, vol. 13, pp. 291-300, 1996).

Particularly, it is known in the art that BMP-2 belonging to the TGF-β superfamily of proteins plays an important role in the development of bone and cartilage, and potentially induce osteoblastic differentiation of a variety of cell types (see "Regulation of human cranial osteoblast phenotype by FGF-2, FGFR-2 and BMP2 signaling", Marie P J, Debiais F, Hay E, 2002). Also, BMP-2 acts to stimulate bone production, and products that induce new bone formation by implanting BMP-2 into collagen sponges are being marketed.

In connection with BMP-2 playing an important role in bone tissue regeneration as described above, various studies have been conducted. Accordingly, it is required to remove proteins or impurities other than BMP-2 from cell culture fluids containing BMP-2 and to obtain BMP-2 from the cell culture fluids in high purity and high yield.

In the prior art, in order to purify BMP-2 from culture fluids of cell, etc. in high purity and obtain it in high yield, several steps of chromatography were combined and performed depending on charges, ligands, the degree of hydrophobicity or size. The type of chromatography used in purification is very diverse, and the purity and yield of BMP-2 greatly vary depending on the type of chromatography. However, as the time for purification of BMP-2 increases and the number of steps for the purification increases, there is a problem in that BMP-2 to be obtained as a final product is degraded by any protease during purification steps or lost during the purification process, resulting in a decrease in the final M yield of BMP-2. Moreover, even if anyone tries to reduce the time and the number of steps for purifying BPM-2 in order to solve this problem, the purity of the finally recovered BMP-2 should not be low.

SUMMARY OF THE INVENTION

In order to solve the problems occurring in the prior art, the present inventors conducted a wide variety of experiments in connection with the chemical and physical characteristics of BMP-2, various types of chromatography, and the resin, column, type and concentration of buffer, washing solution or eluate, and cut-off size of membrane, which are used in each chromatography. As a result, the present inventors have reached the present invention allowing high-purity BMP-2 to be obtained in high yield while reducing the number of purification steps and the purification time.

The present invention relates to a method for purifying a protein belonging to the TGF-β superfamily, preferably a BMP, and more preferably a BMP-2. Particularly, the method according to the present invention is characterized by comprising the following steps:

a) pre-treating a solution containing a protein belonging to the TGF-β superfamily, in which the solution is concentrated using a cut-off membrane filter;

b) subjecting the solution obtained in step a) to hydrophobic interaction chromatography;

c) diafiltering the solution obtained in step b); and d) subjecting the solution obtained in step c) to size exclusion chromatography.

More preferably, step a) of said method further comprises adding NaCl and Tris to the solution concentrated using the cut-off membrane filter, adjusting the solution to a pH 5-9, and then filtering the solution through a filtration filter.

More preferably, NaCl and Tris in step a) are added at concentrations of 0.2-5 M and 5-500 mM, respectively.

More preferably, the cut-off membrane filter used in step a) is a 30 kDa cut-off membrane filter, and the filtration filter has a pore size of 0.1-1.0 µm.

More preferably, the hydrophobic interaction chromatography in step b) is butyl sepharose chromatography.

More preferably, butyl sepharose 4 fast flow resin is used in the butyl sepharose chromatography.

More preferably, the chromatography in step b) comprises equilibrating a column with a buffer containing Tris and NaCl, loading the column with the solution obtained in step a), washing the column with a buffer containing Tris, NaCl and isopropanol, and then eluting the column with a buffer containing Tris, NaCl and isopropanol.

More preferably, the column-equilibrating buffer, column-washing buffer and column-eluting buffer in step b) have a pH 5-9, and the concentration of Tris, NaCl and isopropanol is 5-500 mM, 0.2-5 M and 0.1-50 wt %, respectively.

More preferably, the diafiltration in step c) comprises exchanging and concentrating the solution obtained in step b) with a buffer containing Tris, NaCl, L-arginine and glycerol using a cut-off membrane filter.

More preferably, the buffer that is exchanged in step c) has a pH 5-9, and contains 5-500 mM of Tris, 0.2-5 M of NaCl, 0.2-5 M of L-arginine and 1-50 wt % of glycerol.

More preferably, the cut-off membrane filter used in step c) is a 30 kDa cut-off membrane filter.

More preferably, the size exclusion chromatography in step d) is sephacryl chromatography.

More preferably, sephacryl S-100 resin is used in the sephacryl chromatography.

More preferably, the chromatography in step d) comprises equilibrating a column with a buffer containing Tris and NaCl, loading the column with the solution obtained in step c), and eluting the column with a buffer containing Tris and NaCl.

More preferably, the column-equilibrating buffer and column-eluting buffer in step d) have a pH 5-9, and contain 5-500 mM of Tris and 0.05-5 M of NaCl.

The present invention also relates to a protein purified according to the above-described method.

DESCRIPTION OF DRAWINGS

In FIG. 2, the band corresponding to "M" indicates a marker for determining the molecular weight of a desired protein, and the band corresponding to "B" indicates a BMP-2 eluate recovered through butyl sepharose chromatography.

In FIG. 3, the band corresponding to "M" indicates a marker for determining the molecular weight of a desired protein, and the band corresponding to "B" indicates a BMP-2 eluate recovered through sephacryl chromatography.

In FIG. 4, the band corresponding to "M" indicates a protein marker, the band corresponding to "K" indicates a BMP-2 purified according to the method of the present invention, and the band corresponding to "R" indicates a BMP-2 purchased from R&D Systems, Inc.

DETAILED DESCRIPTION OF THE INVENTION

Figure 1:
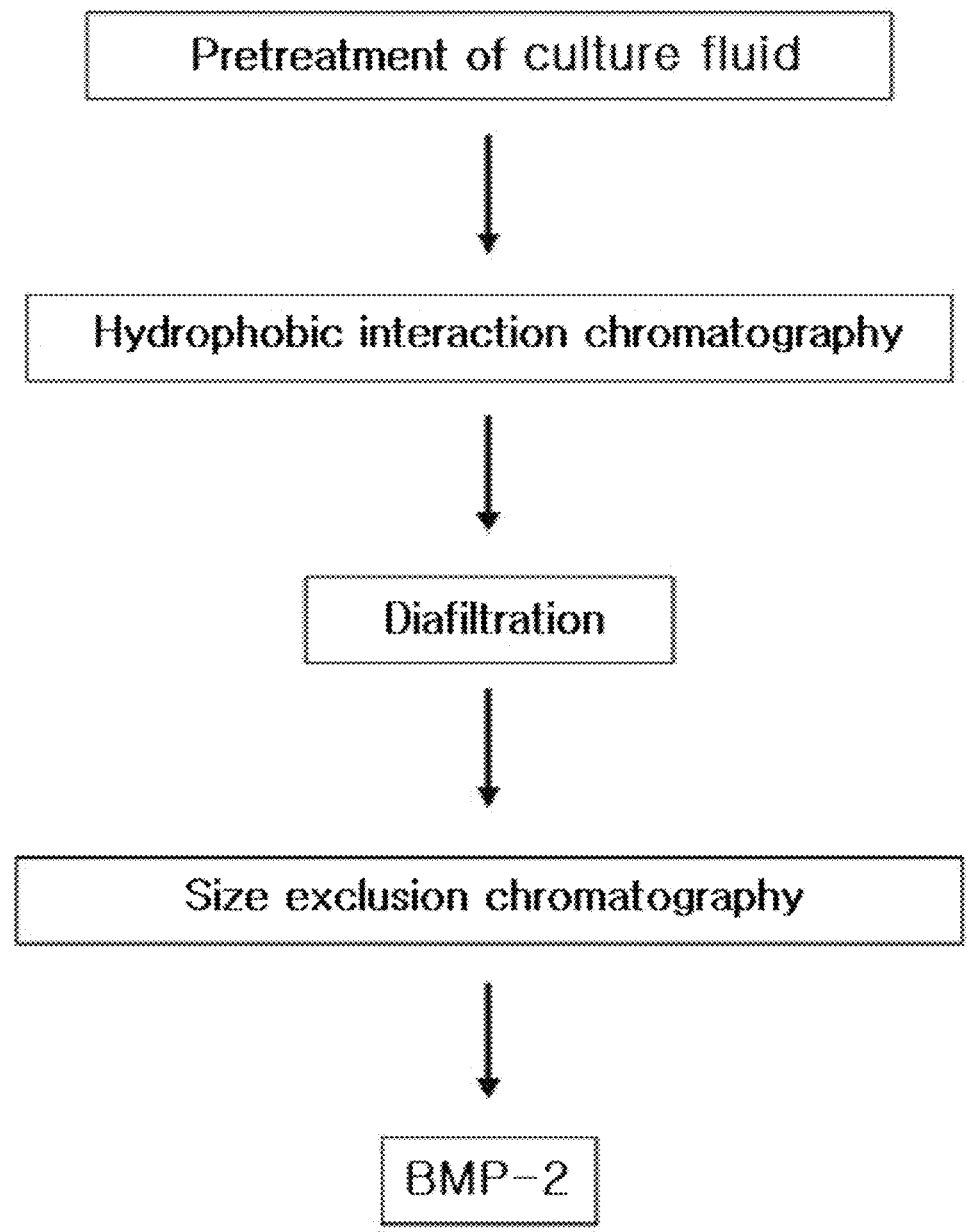
FIG. 1 is a schematic view showing a purification process according to the present invention.

In the present invention, a solution containing a protein belonging to the TGF-β superfamily, which is used as a starting material for purification, is preferably a BMP-containing solution, and more preferably a BMP-2-containing solution. Herein, there is no limitation in the type of BMP-2-producing cells, the type of cell culture medium, culture reagents, and culture conditions. For example, Chinese hamster ovary (CHO) cell culture fluids or *E. coli* culture fluids derived from microorganism, which contain BMP-2 together with other proteins or impurities, may be used as a starting material to be purified in the present invention.

As used herein, the term "Da (Dalton)" used in connection with the cut-off membrane filter is the unit of molecular weight of proteins. For example, if a 30 kDa cut-off membrane filter is used, impurities including proteins having a molecular weight of 30 kDa or less will pass through the membrane filter.

As used herein, the term "hydrophobic interaction chromatography" refers to a separation/purification method that uses a hydrophobic property of proteins. Many various factors, including the salinity, type and pH of a buffer that is used in hydrophobic interaction, influence the ability to separate proteins. Also, because proteins interact with each other under high ionic strength conditions, the ability to separate the proteins is higher when a starting material is purified in previously partially. In the present invention, butyl sepharose chromatography, phenyl sepharose chromatography, octyl sepharose chromatography or the like may be used for purifying BMP-2 in high purity and high yield. Particularly, a chromatographic method that uses butyl sepharose 4 fast flow resin is preferably used.

As used herein, the term "size exclusion chromatography" refers to a method for separating materials according to molecular size using uniformly sized, porous, nonionic gels as a stationary phase. Generally, materials that are smaller than the pore size have a long elution time, because they enter the porous stationary phase and have a longer transit time. On the contrary to this, materials that are larger than the pore size have a short elution time, because they cannot enter the porous stationary phase and thus move fast together with the mobile phase. Accordingly, in the size exclusion chromatography, large-sized materials are eluted fast, and small-sized materials are eluted slowly. In the present invention, size exclusion chromatography, for example sephacryl chromatography, superdex chromatography or sephadex chromatography is preferably used for purifying BMP-2 in high purity and high yield. Particularly, a chromatographic method that uses sephacryl s-100 resin is preferably used.

In chromatography, pH is an important factor determining the stabilization of proteins.

Pressure and flow rate are important factors that determine the interaction between a desired protein and a column and the ability to separate the desired protein.

Conductivity indicates the concentration of an electrolyte in a solvent, which influences whether the desired protein is bound to or separated from the column.

Column volume (CV) indicates the volume of a packed column, and the purification volume is determined according to the CV.

Equilibration is a process of making a buffer in a column equal to a buffer composition of a sample before being loaded into the column, in order to prevent a protein of interest from being agglomerated or losing its activity by environmental changes. The composition of a buffer that is used for equilibration varies depending on the type of desired protein.

Loading is a process of injecting a sample into a column. It is general to load about 30-40% of the column volume, but the present inventors made it possible to load about 200% or more of the column volume by controlling the detailed conditions of chromatography.

Washing is a process of removing impurities other than a desired protein. The concentrations and components of a buffer that is used for washing vary depending on the type of protein to be purified.

Elution is a process of separating a desired protein from a column. In case that the concentrations and components of a buffer are not suitable, there is a problem in that the purity of the desired protein is reduced, because a large amount of impurities are simultaneously eluted. For this reason, the concentrations and components of a buffer that is used for elution are changed depending on the type of protein to be purified.

Diafiltration is a combined method of dialysis and ultrafiltration. It is generally used to remove only some solutes from a fluid containing a solvent and two or more solutes having different molecular sizes.

In diafiltration, feed pump speed indicates the pump speed at which a buffer is flowed into a membrane filter. The feed pump speed is an important factor that determines the yield of BMP-2.

Feed pressure indicates the pressure of an injection line, which is caused by the feed pump.

Retentate pressure indicates the pressure of a solvent which is returned without passing through a membrane filter, and it is an important factor determining the yield of BMP-2.

Permeate pressure indicates the pressure of a solvent which passes through a membrane filter, and it is an important factor determining the yield of BMP-2.

Accordingly, feed pump speed, feed pressure, retentate pressure and permeate pressure should be comprehensively considered to determine their suitable values in order to purify BMP-2 in high yield and purity.

As used herein, the term "SDS-PAGE" is an abbreviation for sodium dodecyl sulfate polyacrylamide gel electrophoresis. It is a technique of separating proteins according to electrophoretic mobility (for example, factors such as the molecular weight or length of a polypeptide chain). In this case, proteins having low molecular weights show long migration distances, and when a Rf value is obtained using a molecular weight marker, the molecular weight of a desired protein can be determined or the desired protein can be identified.

As used herein, the term "Tris" is an abbreviation for an organic compound known as tris(hydroxymethyl)aminomethane having the formula $(HOCH_2)_3CNH_2$.

EXAMPLES

Hereinafter, the method of the present invention for purifying BMP-2 among proteins belonging to the TGF-β superfamily will be described in detail with reference to the following examples. It is to be understood, however, that these examples are for illustrative purposes only and are not to be construed to limit the scope of the present invention. In addition, it is to be understood that those ordinarily skilled in the art may make various modifications to the examples within the scope of the present invention.

1. Step of Pre-Treating Culture Fluids

30 L of Chinese hamster ovary (CHO) cell culture fluid containing BMP-2 was concentrated to about 3 L using a 30 kDa cut-off membrane filter. Then, NaCl (1 M) and Tris (50 mM) were added to the culture fluid which was then adjusted to a pH of about 7.0. After that, the culture fluid was filtered through a filtration filter having a pore size of 0.2 μm.

Unlike conventional processes of purifying BMP-2, the BMP-2-containing culture fluid was concentrated about 10-fold before the culture fluid was subjected to chromatography in the present invention, whereby the amount of materials added thereto was reduced to ¹⁄₁₀. This could shorten the time required for the subsequent hydrophobic interaction chromatography. Also, this could solve the problem that the degree of degradation of BMP-2 increases as the purification time is delayed. Thus, in the present invention, the yield of the finally obtained BMP-2 was increased.

In conventional processes of purifying BMP-2, it is usual to filter a BMP-2-containing culture fluid directly, but in the filtration step of the present invention, the filtration was performed after adding NaCl and Tris to the BMP-2-containing culture fluid and adjusting the pH of the culture fluid to about 7.0.

2. Step of Performing Hydrophobic Interaction Chromatography

The filtered solution was subjected to a hydrophobic interaction chromatography process using butyl sepharose 4 fast flow resin. In this step, the chromatography column was equilibrated with 3 CV (column volume) of a buffer containing 50 mM Tris and 1 M NaCl (pH: about 7.0). Then, the filtered solution was loaded into the column up to about 2 CV of the packed column volume. Then, the column was washed with 3 CV of a buffer containing 50 mM Tris, 850 mM NaCl and 3-4 wt % isopropanol (pH: about 7.0). After that, the BMP-2-containing solution was eluted with 2 CV of a buffer containing 50 mM Tris, 600 mM NaCl and 10-15 wt % isopropanol (pH: about 7.0).

Herein, the butyl sepharose chromatography is a process for removing most impurity proteins other than BMP-2 from the culture fluid. The conditions of chromatography vary depending on the type of protein, but in the present invention, the composition and concentration of the buffer used in the butyl sepharose chromatography were optimized, thereby purifying BMP-2 in high yield and high purity.

The specific conditions in which the butyl sepharose chromatography was performed are shown in Table 1 below.

TABLE 1

Operating parameters of butyl sepharose chromatography

| | Parameter | Desired range |
|---|---|---|
| All processes | Pressure | ≤10 psi |
| | pH | 7.0 ± 0.2 |
| Equilibration | Flow rate | 60 cm/h |
| | Volume | 3 CV |
| | Conductivity | 89-90 mS/cm |
| Loading | Flow rate | 30 cm/h |
| | Volume | 2 CV |
| | Conductivity | 80-90 mS/cm |
| Washing | Flow rate | 60 cm/h |
| | Volume | 3 CV |
| | Conductivity | 65-66 mS/cm |
| Elution | Flow rate | 30 cm/h |
| | Volume | 2 CV |
| | Conductivity | 45-46 mS/cm |

Figure 2:
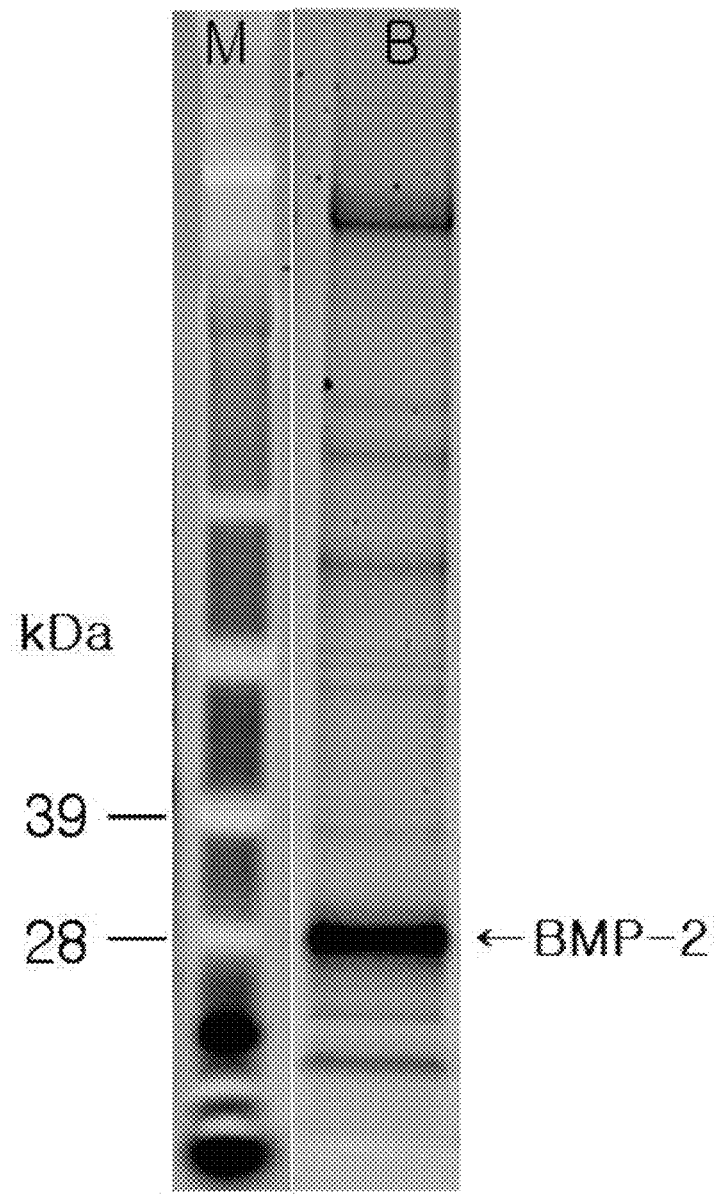
FIG. 2 shows the result of SDS-PAGE analysis of a BMP-2 eluate recovered from a butyl sepharose chromatography step.

FIG. 2 shows the result of SDS-PAGE analysis of a BMP-2 eluate recovered from the butyl sepharose chromatography step. In FIG. 2, the band corresponding to "M" indicates a marker for determining the molecular weight of a desired protein, and the band corresponding to "B" indicates a BMP-2 eluate recovered through butyl sepharose chromatography. In the band corresponding to "B", the portion pointed out by the arrow indicates the BMP-2 to be purified in the present invention.

The BMP-2 eluate recovered from the butyl sepharose chromatography step was analyzed and, as a result, the yield of BMP-2 was about 95% and the purity of BMP-2 was about 85%.

3. Step of Performing Diafiltration

The BMP-2-containing solution eluted by the hydrophobic interaction chromatography was exchanged and concentrated with a buffer containing 50 mM Tris, 600 mM NaCl, 0.5 M L-arginine and 5 wt % glycerol (pH: about 7.0) using a 30 kDa cut-off membrane filter, thus obtaining about 20 mL of a solution.

Herein, diafiltration is a preparatory step for size exclusion chromatography after the completion of the hydrophobic interaction chromatography, in which the buffer composition of the sample is optimized to obtain a high-purity BMP-2.

In the conventional BMP-2 purification process, a 10 kDa cut-off membrane filter was usually used. However, if this 10 kDa cut-off membrane filter is used, there is a problem in that the solution contains impurities such as proteins having a molecular weight of 10 kDa or more in addition to a BMP-2 intended to be purified, and for this reason, additional purification steps and time are further required. On the contrary, the diafiltration step of the present invention uses a 30 kDa cut-off membrane filter to remove impurities, such as proteins having a molecular weight of 30 kDa or less, from the BMP-2-containing solution. Thus, the 30 kDa cut-off membrane filter used in the diafiltration step of the present invention has an advantage in that it can remove a large amount of impurities compared to the 10 kDa cut-off membrane filter.

Herein, because the BMP-2 protein to be purified in the present invention has a molecular weight of about 28-32 kDa, if the 30 kDa cut-off membrane filter is used, a large amount of BMP-2 can be lost. For this reason, the 10 kDa cut-off membrane filter was used instead of the 30 kDa cut-off membrane filter in the prior art. However, the present inventors controlled parameters, such as the type and concentration of buffer, feed pump speed and feed pressure, to the optimum conditions, whereby the loss of BMP-2 could be prevented while removing impurities having a molecular weight of 30 kDa or less using the 30 kDa cut-off membrane filter. The parameters used in the diafiltration step of the present invention are shown in Table 2 below.

TABLE 2

| Operating parameters of diafiltration (30 kDa cut-off) | |
|---|---|
| Parameter | Desired range |
| Feed pump speed | 20 mL/min |
| Feed pressure | 0.8-1.2 psi |
| Retentate pressure | 0.1-0.2 psi |
| Permeate pressure | 0.1-0.2 psi |
| TMP (trans-membrane pressure) | 0.4-0.6 psi |

4. Step of Performing Size Exclusion Chromatography

The concentrated BMP-2-containing solution was subjected to a size exclusion chromatography process using sephacryl s-100 resin. In this step, the chromatography column was equilibrated with 1 CV of a buffer containing 50 mM Tris and 0.6 M NaCl (pH: about 7.0). Then, the concentrated BMP-2-containing solution was loaded into the column up to 4% of the packed column volume. Then, the column was eluted with 1 CV of a buffer containing 50 mM Tris and 0.6 M NaCl (pH: about 7.0).

The conditions in which size exclusion chromatographs is performed vary depending on the type of protein, and the purity of protein purified varies depending on the buffer composition of sample injected into the column and the buffer composition eluted out of the column. Particularly preferred parameters used in the sephacryl chromatography in the present invention are shown in Table 3 below.

TABLE 3

| Operating parameters of sephacryl chromatography | | |
|---|---|---|
| | Parameter | Desired range |
| All processes | Pressure | ≤15 psi |
| | pH | 7.0 ± 0.2 |
| | Flow rate | 10-30 cm/h |
| Equilibration | Volume | 1 CV |
| | Conductivity | 65-66 mS/cm |
| Elution | Volume | 1 CV |
| | Conductivity | 65-66 mS/cm |

Figure 3:
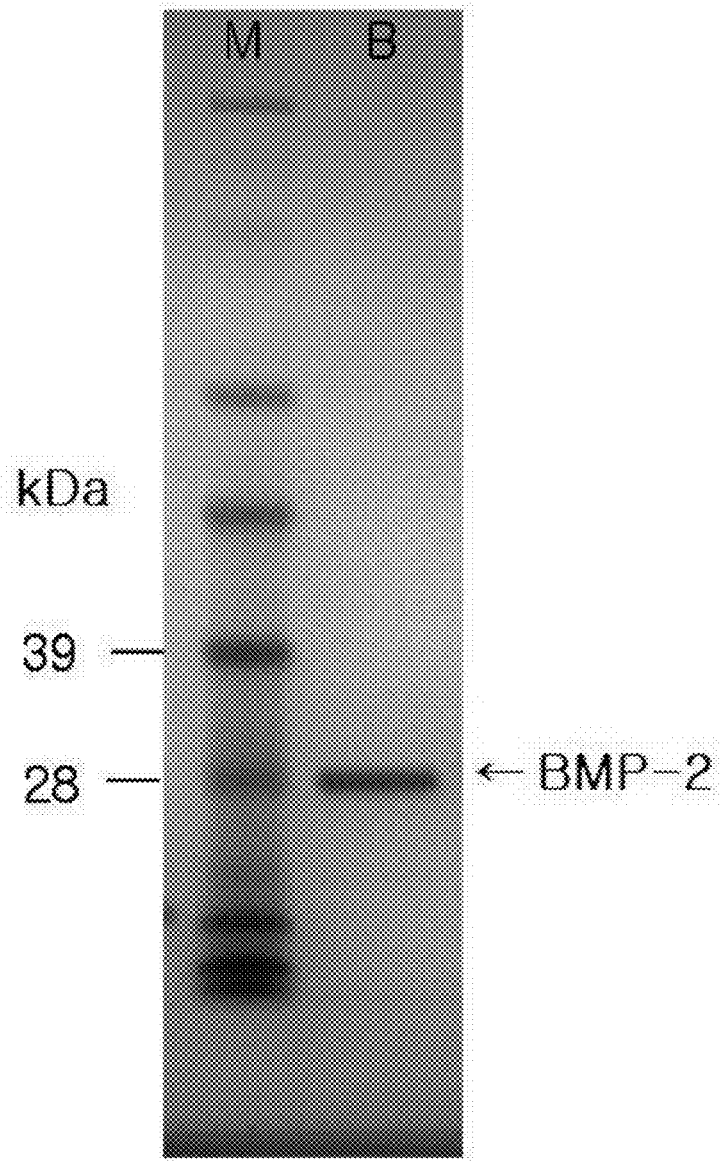
FIG. 3 shows the result of SDS-PAGE analysis of a BMP-2 eluate recovered from a sephacryl chromatography step.

FIG. 3 shows the result of SDS-PAGE analysis of the BMP-2 eluate recovered from the sephacryl chromatography step. In FIG. 3, the band corresponding to "M" indicates a marker for determining the molecular weight of a desired protein, and the band corresponding to "B" indicates the BMP-2 eluate recovered through sephacryl chromatography. In the band corresponding to "B", the portion pointed out by the arrow indicates the BMP-2 M to be purified in the present invention.

The BMP-2 eluate purified from the sephacryl chromatography step was analyzed and, as a result, the yield of BMP-2 was about 88% or more and the purity of BMP-2 was about 95%.

The yield and purity obtained by quantitatively analyzing the BMP-2 determined from each of the BMP-2 purification steps of the present invention are shown in Table 4 below.

TABLE 4

| Yield and purity of BMP-2 recovered from each of the purification steps of the present invention | | |
|---|---|---|
| Purification steps | Yield (%) of BMP-2 | Purity (%) of BMP-2 |
| Cell culture fluid | 100 | 5.7 |
| Hydrophobic interaction chromatography | 95 | 85 |
| Diafiltration | 95 | 85 |
| Size exclusion chromatography | 88 | 95 |
| Finally purified BMP-2 | 88 | 95 |

5. Experiment for Identification and for Comparison of Purity of BMP-2 Purified According to the Method of the Present Invention In order to confirm whether the protein purified according to the method of the present invention is BMP-2 and to compare the purity of the BMP-2 purified according to the present invention with the purity of a BMP-2 purchased from R&D Systems, Inc., Western blot analysis was performed in the following manner.

(1) 1 μg of the finally purified rhBMP-2 is mixed with 4× SDS-PAGE sample buffer at a ratio of 1:3.
(2) The mixed sample is boiled at 70° C. for 10 minutes.
(3) The sample is centrifuged at 10,000×g for 10 minutes.
(4) The centrifuged supernatant is loaded on 4-12% Bis-Tris polyacrylamide gel.
(5) Then, electrophoresis is performed at a constant voltage of 100 V for 2 hours.

(6) The electrophoresed protein is transferred onto a PVDF membrane at 100 V for 1 hour.

(7) The portion of the PVDF membrane, to which the protein, is not attached, is blocked with 5% skim milk-containing TBST for 30 minutes.

(8) The membrane is allowed to react for 2 hours with TBST containing primary antibody diluted at 3000:1 and 1% skim milk. Herein, the primary antibody is an anti-mouse IgG that binds specifically to BMP-2 and is originated from mouse.

(9) The membrane is washed 4 times with TBST for 15 minutes each time.

(10) The membrane is allowed to react for 30 minutes with TBST containing secondary antibody diluted at 5000:1 and 1% skim milk. Herein, the secondary antibody is a HRP-conjugated goat anti-mouse IgG that binds to the primary antibody and is originated from goat. HRP, i.e. an enzyme catalyzing a reaction with the substrate that causes the color change is attached to said secondary antibody.

(11) The membrane is washed 4 times with TBST for 15 minutes each time.

(12) A developing solution is added to the membrane, and then it is analyzed by an image analyzer.

Figure 4:
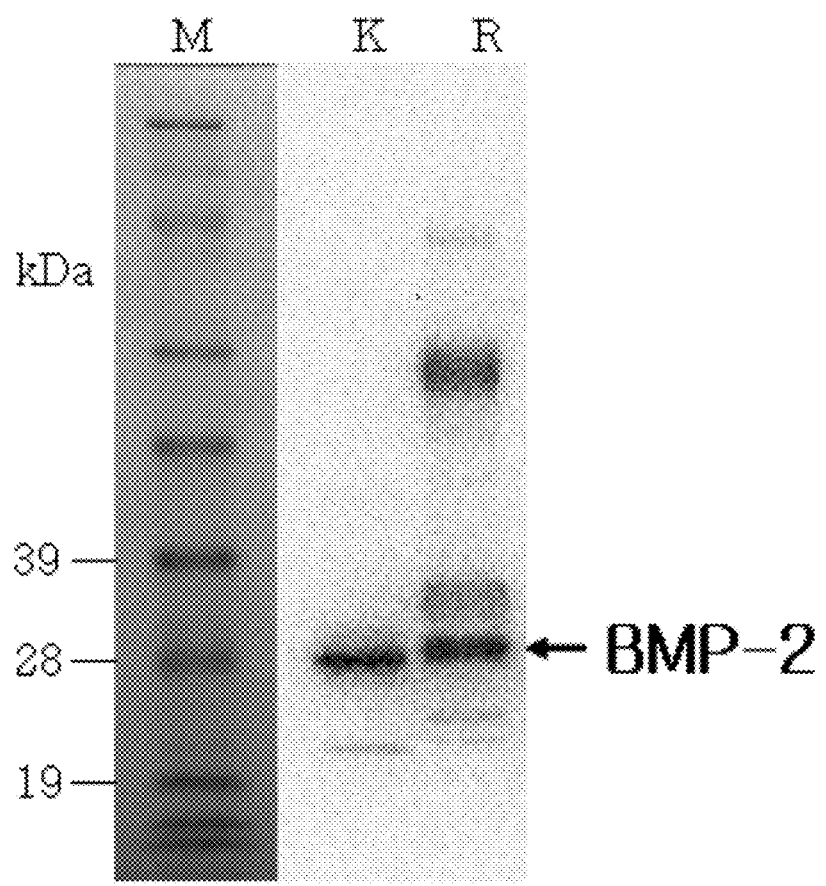
FIG. 4 shows the result of Western blot analysis of a BMP-2 purified according to the method of the present invention and a BMP-2 purchased from R&D Systems, Inc.

FIG. 4 shows the result of the Western blot analysis. In FIG. 4, the band corresponding to "M" indicates a protein marker, the band corresponding to "K" indicates a BMP-2 purified according to the present invention, and the band corresponding to "R" indicates a BMP-2 purchased from R&D Systems, Inc. From the results in FIG. 4, it was confirmed that the protein purified according to the present invention was BMP-2. In addition, the BMP-2 purified according to the present invention had a significantly high purity compared to the BMP-2 of R&D Systems, Inc.

As described above, according to the method of the invention for purifying a protein belonging to the TGF-β to superfamily, particularly BMP-2, the number of purification steps is reduced and the purification process is simplified, compared to the conventional method for purifying BMP-2. Thus, the time required for purification of BMP-2 can be shortened and the purification cost can be reduced. Also, the present invention solves the problem that as the time for purification of BMP-2 increases and the number of purification steps increases, BMP-2 is degraded by protease or lost during purification steps, resulting in a decrease in the final yield of BMP-2. Thus, the method of the invention increases the final yield of BMP-2.

In addition, according to the method of the invention, although the number of purification steps is reduced, a high purity of BMP-2 can be finally obtained in high yield by optimizing and using filtrations and chromatographies, and columns, types and concentrations of buffers, and a cut-off size of membrane used in diafiltration, which are different from those of the conventional BMP-2 purification method.

What is claimed is:

1. A method for purifying bone morphogenetic 2 (BMP-2), comprising the steps of:
   a) pre-treating by concentrating a solution containing BMP 2 using a 30 kDa cut-off membrane filter;
   b) subjecting the solution obtained in step a) to hydrophobic interaction chromatography;
   c) diafiltering the solution obtained in step b); and
   d) subjecting the solution obtained in step c) to size exclusion chromatography to obtain purified BMP-2.

2. The method of claim 1, wherein step a) further comprises adding NaCl and Tris to the solution concentrated using the cut-off membrane filter, adjusting the solution to a pH 5-9, and then filtering the solution through a filtration filter.

3. The method of claim 2, wherein NaCl and Tris in step a) are added at concentrations of 0.2-5 M and 5-500 mM, respectively.

4. The method of claim 2, wherein the filtration filter has a pore size of 0.1-1.0 μm.

5. The method of claim 1, wherein the hydrophobic interaction chromatography in step b) is butyl sepharose chromatography.

6. The method of claim 5, wherein butyl sepharose 4 fast flow resin is used in the butyl sepharose chromatography.

7. The method of claim 5, wherein the chromatography in step b) comprises equilibrating a column with a buffer containing Tris and NaCl, loading the column with the solution obtained in step a), washing the column with a buffer containing Tris, NaCl and isopropanol, and then eluting the column with a buffer containing Tris, NaCl and isopropanol.

8. The method of claim 7, wherein the column-equilibrating buffer, column-washing buffer and column-eluting buffer in step b) have a pH 5-9, and the concentration of Tris, NaCl and isopropanol is 5-500 mM, 0.2-5 M and 0.1-50 wt %, respectively.

9. The method of claim 1, wherein the diafiltration in step c) comprises exchanging and concentrating the solution obtained in step b) with a buffer containing Tris, NaCl, L-arginine and glycerol using a cut-off membrane filter.

10. The method of claim 9, wherein the buffer that is exchanged in step c) has a pH 5-9, and contain 5-500 mM of Tris, 0.2-5 M of NaCl, 0.2-5 M of L-arginine and 1-50 wt % of glycerol.

11. The method of claim 9, wherein the cut-off membrane filter used in step c) is a 30 kDa cut-off membrane filter.

12. The method of claim 1, wherein the size exclusion chromatography in step d) is sephacryl chromatography.

13. The method of claim 12, wherein sephacryl s-100 resin is used in the sephacryl chromatography.

14. The method of claim 12, wherein the chromatography in step d) comprises equilibrating a column with a buffer containing Tris and NaCl, loading the column with the solution obtained in step c), and then eluting the column with a buffer containing Tris and NaCl.

15. The method of claim 14, wherein the column-equilibrating buffer and column-eluting buffer in step d) have a pH 5-9, and contain 5-500 mM of Tris and 0.05-5 M of NaCl.

* * * * *

UNITED STATES PATENT AND TRADEMARK OFFICE
CERTIFICATE OF CORRECTION

| | | |
|---|---|---|
| PATENT NO. | : 8,648,178 B2 | |
| APPLICATION NO. | : 13/142928 | |
| DATED | : February 11, 2014 | |
| INVENTOR(S) | : Shim et al. | |

It is certified that error appears in the above-identified patent and that said Letters Patent is hereby corrected as shown below:

In the Claims

Column 9, Line 55, Claim 1, the word "bone morphogenetic 2" should read "bone morphogenetic protein 2".

Column 10, Lines 1-2, Claim 1, the word "BMP 2" should read "BMP-2".

Signed and Sealed this
Twenty-ninth Day of July, 2014

Michelle K. Lee
*Deputy Director of the United States Patent and Trademark Office*